United States Patent [19]

Nawroth et al.

[11] Patent Number: 4,885,277

[45] Date of Patent: Dec. 5, 1989

[54] ANTICOAGULANT THERAPY

[75] Inventors: Peter P. Nawroth, Bornshof, Fed. Rep. of Germany; David M. Stern, Great Neck, N.Y.; George D. Wilner, St. Louis, Mo.

[73] Assignee: Oklahoma Medical Research Foundation, Oklahoma City, Okla.

[21] Appl. No.: 118,316

[22] Filed: Nov. 6, 1987

Related U.S. Application Data

[63] Continuation-in-part of Ser. No. 916,773, Oct. 9, 1986, abandoned.

[51] Int. Cl.$^4$ .................. A61K 37/02; C07K 7/08
[52] U.S. Cl. .................................. 514/15; 514/17; 514/802; 530/328; 530/330; 530/800
[58] Field of Search ............... 530/328, 393, 384, 350, 530/330, 800; 514/17, 15, 822, 802

[56] References Cited

U.S. PATENT DOCUMENTS

| | | | |
|---|---|---|---|
| 3,560,475 | 2/1971 | Fekete et al. | 530/384 |
| 3,826,793 | 7/1974 | Blomback et al. | 260/112.5 |
| 4,046,722 | 9/1977 | Rowland | 260/112 |
| 4,081,432 | 3/1978 | Delente et al. | 530/384 |
| 4,455,290 | 6/1984 | Olexa et al. | 424/1.1 |
| 4,461,724 | 7/1984 | Konishi | 260/112.5 |
| 4,578,079 | 3/1986 | Ruoslahti et al. | 623/11 |
| 4,585,740 | 4/1986 | Vanderlaan | 436/537 |
| 4,590,168 | 5/1986 | Sytkowski et al. | 530/329 |
| 4,686,283 | 8/1987 | Dextor, Jr. et al. | 530/328 |

OTHER PUBLICATIONS

Peptide Hormones, Rudinger, pp. 1–7.
Solid-Phase Peptide Synthesis III, An Improved Synthesis of Bradykinin, Merrifield, Biochem., 3:1385, 1964.
Isolation and Characterization of Bovine Factor IX, (Christmas Factor), Fujikawa et al., Biochem., 12:4938–4945, 1973.
The Mechanism of Activation of Bovine Factor IX, (Christmas Factor), by Bovine Factor XI$_a$, (Activated Plasma Thromboplastin Antecedent), Fujikawa et al., Biochem., 13:4508–4516, 1974.
Immunochemical Studies of Human Fibrinopeptide A Using Synthetic Peptide Homologues, Wilner et al., Biochem., 15:1209, 1976.
In Vitro and In Vivo Correlation of Clotting Protease Activity: Effect of Heparin, Gitel et al., Proc. Natl. Acad. Sci. USA, 74:3028, 1977.
Activation of Factor IX by the Reaction Product of Tissue Factor and Factor VII: Additional Pathway for Initiating Blood Coagulation, Osterud and Rapaport, Proc. Natl. Acad. Sci. USA, 74:5260, 1977.
Comparison of Amino Acid Sequence of Bovine Coagulation Factor IX, (Christmas Factor), with that of Other Vitamin D-dependent Plasma Proteins, Katayama et al., Proc. Natl. Acad. Sci. USA, 76:4990, 1979.
The Role of Phospholipid and Factor VIII$_a$ in the Activation of Bovine Factor X, van Dieijen et al., J. Biol. Chem., 256:3433, 1981.
Molecular Cloning of the Gene for Human Antihaemophilic Factor IX, Choo et al., Nature, 299:178–180, 1982.
Isolation and Characterization of a cDNA Coding for Human Factor IX, Kurachi and Davie, Proc. Natl. Acad. Sci. USA, 79:6461–6464, 1982.
Isolation of a Human Anti-haemophilic Factor IX cDNA Clone Using a Unique 52-base Synthetic Oligonucleotide Probe Deduced from the Amino Acid Sequence of Bovine Factor IX, Jaye et al., Nucl. Acids Res., 11:2325–2335, 1983.
Binding of Factors IX and IX$_a$ to Cultured Vascular Endothelial Cells, Stern et al., Proc. Natl. Acad. Sci. USA, 80:4119–4132, 1983.
Binding of Coagulation Factors IX and X to the Endothelial Cell Surface, Heimark and Schwartz, Biochem. Biophys. Res. Comm., 111:723–731, 1983.
$S_N2$ Deprotection of Synthetic Peptides with a Low Concentration of HF in Dimethyl Sulfide: Evidence and Application in Peptide Synthesis, Tam et al., J. Am. Chem. Soc., 105:6442, 1983.
A Coagulation Pathway on Bovine Aortic Segments Leading to Generation of Factor X$_a$ and Throbin, Stern et al., J. Clin. Invest., 74:1910–1921, 1984.
Activation of Factor IX Bound to Cultured Bovine Aortic Endothelial Cells, Stern et al., Proc. Natl. Acad. Sci. USA, 81:913–917, 1984.
The Binding of Factor IX$_a$ to Cultured Bovine Aortic Endothelial Cells, Stern et al., J. Biol. Chem., 260:6717–6722, 1985.
A Pathway of Coagulation on Bovine Capillary Endothelial Cells, Nawroth et al., Brit. J. Haematol., 63:309–320, 1986.
Anticoagulant and Antithrombotic Properties of a Y-Carboxyglutamic Acid-Rich Peptide Derived From the Light Chain of Blood Coagulation Factor X, Nawroth et al., Thromb. Res., 44:625–637, 1986.
The EGF Domain of the Factor IX Molecule is Involved in Factor IX–Endothelial Cell Interaction, Nawroth et al., 59th Scientific Sessions, American Heart Association, Circulation 74, (Suppl. II):232, (Abstract No. 929), 1986.

Primary Examiner—Delbert R. Phillips
Assistant Examiner—T. Wessendorf
Attorney, Agent, or Firm—Kilpatrick & Cody

[57] ABSTRACT

A composition and method for treating thrombotic disorders. The composition comprises a peptide comprising an amino acid sequence corresponding to the sequence of the amino acid residues in the EGF domain of Factor IX, or a subsequence thereof. Such peptides compete with coagulation Factors IX and IXa for endothelial binding cites and thereby inhibit thrombosis formation.

6 Claims, No Drawings

ANTICOAGULANT THERAPY

This application is a continuation-in-part of U.S. patent application Ser. No. 916,773, filed Oct. 9, 1986, entitled "ANTICOAGULATION THERAPY" now abandoned. This application is related to co-pending U.S. patent application Ser. No. 930,588, filed Nov. 13, 1986, entitled "PEPTIDES FROM THE FACTOR IX MOLECULE WHICH SPECIFICALLY BLOCK THE BINDING AND FUNCTION OF FACTOR IX TO THE ENDOTHELIAL CELL SURFACE AND PREVENT THROMBOSIS" now abandoned.

FIELD OF THE INVENTION

The present invention relates generally to anticoagulant therapy, and more particularly to use of a peptide comprising an amino acid sequence which corresponds to at least a portion of the Factor IX molecule.

SUMMARY OF THE INVENTION

The present invention comprises a peptide comprising a sequence of amino acid residues substantially corresponding to the sequence of amino acid residues 43 through 136 of Factor IX, or a subsequence thereof. The peptide is characterized by an ability to selectively interact with endothelial cellular receptors for Factor IX and Factor IXa. The present invention further comprises a pharmaceutical composition comprising such a peptide and a pharmaceutically acceptable carrier. The present invention further comprises a method for treating thrombotic disorders in subjects in need of such therapy comprising administering to the subject a therapeutically effective amount of the pharmaceutical composition.

DESCRIPTION OF THE PREFERRED EMBODIMENT

Under normal conditions, an injury to endothelium, the cells lining the blood vessels, triggers a clotting response to prevent extravasation. The normal clotting response requires the interaction of several factors in a so-called "cascade mechanism". One of these is Factor IX, which is a Vitamin K-dependent plasma glycoprotein.

During the normal process of hemostasis, Factor IX is converted to an enzyme form, Factor IXa, which in turn activates Factor X in the presence of Factor VIII, calcium and an appropriate cellular or phospholipid surface. (van Dieijan, et al., J. Biol. Chem., 256, pp. 3433–3441 [1981]). Thus, Factors IX and IXa play an essential role in the normal clotting response.

However, Factor IX also has been implicated in thrombosis, the pathological formation of intravascular blood clots. (Gitel, et al., Proc. Natl. Acad. Sci. U.S.A., 74, pp. 3028–3032 [1977]). Thrombosis formation leads to myocardial infarction, stroke and other diseases and disorders involving thrombotic and thrombo-embolic mechanisms. These are referred to herein collectively as thrombotic disorders. Specifically, recent studies have indicated that thrombosis may occur at least partly as a result of Factor IX binding to cellular receptors in the endothelium. (Stern, et al., Proc. Natl. Acad. Sci. U.S.A., 80, pp. 4119–4123 [1983]; Heimark, et al., Biochem. Biophys. Res. Comm. III, pp. 723–731 [1983]; Stern, et al., J. Clin. Invest., 74, pp. 1910–1021 [1984]; Stern, et al., Proc. Natl. Acad. Sci. U.S.A., 81, pp. 913–917 [1984]; Stern, et al., J. Biol. Chem., 260, pp. 6717–6722 [1985]).

The peptides of the present invention compete with Factors IX and IXa for their binding sites on intact (uninjured) endothelium. In this way, the peptides of this invention prevent thrombosis without affecting normal hemostatic mechanisms.

Human and bovine Factor IX each comprise a sequence of 416 amino acid residues which have been identified. (Katayama, et al., Proc. Natl. Acad. Sci. U.S.A., 76, pp. 4990–4994 [1979]; Choo, et al., Nature, 299, pp. 178–180 [1982]; Kurachie, et al., Proc. Natl. Acad. Sci. U.S.A., 79, pp. 6461–6464 [1982]; Jaye, et al., Nucl. Acids Res. II, pp. 2325–2335 [1983]). A portion of the Factor IX molecule, residues 47–136, is similar to a naturally occurring hormone called Epidermal Growth Factor ("EGF"), which also is a polypeptide. The peptides of this invention comprise a sequence of amino acid residues which substantially corresponds to the amino acid sequence of the EGF domain of Factor IX or a subsequence thereof.

The peptides of this invention may be used in a pharmaceutical composition to treat thrombotic disorders in subjects in need of such therapy. This therapy may be used in conjunction with surgical treatment and other medical treatment of such disorders, such as anticoagulant and fibrinolytic therapy.

Thus, in accordance with the present invention, a peptide first is prepared. The peptide comprises a sequence of amino acid residues which substantially corresponds to the sequence of amino acid residues 43 through 136 of Factor IX or a subsequence thereof. The amino acid sequence of the EGF domain of bovine Factor IX is shown in FIG. 1. The amino acid sequence of human Factor IX is shown in FIG. 2.

The peptides of the present invention are characterized as being capable of selectively interacting with endothelial receptors for Factor IX and IXa, thereby preventing the binding of Factor IX and IXa thereto and inhibiting thrombosis formation. Preferred peptides include the pentapeptide comprising the sequence Asp-Gly-Asp-Gln-Cys, which corresponds to residues 47–51 (the first five residues) of the EGF domain of the human and bovine Factor IX molecule, and the nonapeptide comprising the sequence Lys-Gln-Tyr-Val-Asp-Gly-Asp-Gln-Cys, which corresponds to residues 43–51 of the human Factor IX molecule. The first four residues of this nonapeptide correspond to the four residues immediately preceding the EGF domain.

As used herein, the term "substantially corresponds" denotes a sequence similar enough to the EGF domain sequence, or a subsequence thereof, to compete with the Factor IX/IXa molecule for endothelial binding sites, and thereby to inhibit thrombosis formation. Absolute identity between the amino acid sequence of the peptide and the selected fragment of the EGF domain of the Factor IX molecule is not required. Also, it is to be understood that the peptide of this invention may include other amino acid residues in addition to the residue sequence corresponding to the EGF domain or a fragment thereof.

FIG. 1

|    |    |    |    |    |    | 43  | 44  | 45  | 46  |
|----|----|----|----|----|----|-----|-----|-----|-----|
|    |    |    |    |    |    | Lys | Gln | Tyr | Val |
| 47 | 48 | 49 | 50 | 51 | 52 | 53  | 54  | 55  | 56  |
| Asp | Gly | Asp | Gln | Cys | Glu | Ser | Asn | Pro | Cys |
| 57 | 58 | 59 | 60 | 61 | 62 | 63  | 64  | 65  | 66  |
| Leu | Asn | Gly | Gly | Met | Cys | Lys | Thr | Asp | Ile |

FIG. 1-continued

| 67 | 68 | 69 | 70 | 71 | 72 | 73 | 74 | 75 | 76 |
|----|----|----|----|----|----|----|----|----|----|
| Asn | Ser | Tyr | Glu | Cys | Trp | Cys | Gln | Ala | Gly |
| 77 | 78 | 79 | 80 | 81 | 82 | 83 | 84 | 85 | 86 |
| Phe | Glu | Gly | Thr | Asn | Cys | Glu | Leu | Asp | Ala |
| 87 | 88 | 89 | 90 | 91 | 92 | 93 | 94 | 95 | 96 |
| Thr | Cys | Ser | Ile | Lys | Asn | Gly | Arg | Cys | Lys |
| 97 | 98 | 99 | 100 | 101 | 102 | 103 | 104 | 105 | 106 |
| Gln | Phe | Cys | Lys | Arg | Asp | Thr | Asp | Asn | Lys |
| 107 | 108 | 109 | 110 | 111 | 112 | 113 | 114 | 115 | 116 |
| Val | Val | Cys | Ser | Cys | Thr | Asp | Gly | Tyr | Arg |
| 117 | 118 | 119 | 120 | 121 | 122 | 123 | 124 | 125 | 126 |
| Leu | Ala | Glu | Asp | Gln | Lys | Ser | Cys | Glu | Pro |
| 127 | 128 | 129 | 130 | 131 | 132 | 133 | 134 | 135 | 136 |
| Ala | Val | Pro | Phe | Pro | Cys | Gly | Arg | Val | Ser |

Sequence of amino acid residues 43-136 which comprises the EGF domain (47-136) of bovine Factor IX and the four residues(43-46) immediately preceding this portion. The amino acids aredesignated by their common three letter abbreviations. Above each amino acid designation is the number that the residueoccupies in the sequence of the entire Factor IX molecule.

FIG. 2

|   |   |   |   |   |   | 43 | 44 | 45 | 46 |
|----|----|----|----|----|----|----|----|----|----|
|   |   |   |   |   |   | Lys | Gln | Tyr | Val |
| 47 | 48 | 49 | 50 | 51 | 52 | 53 | 54 | 55 | 56 |
| Asp | Gly | Asp | Gln | Cys | Glu | Ser | Asn | Pro | Cys |
| 57 | 58 | 59 | 60 | 61 | 62 | 63 | 64 | 65 | 66 |
| Leu | Asn | Gly | Gly | Ser | Cys | Lys | Asp | Asp | Ile |
| 6 | 68 | 69 | 70 | 71 | 72 | 73 | 74 | 75 | 76 |
| Asn | Ser | Tyr | Glu | Cys | Trp | Cys | Pro | Phe | Gly |
| 77 | 78 | 79 | 80 | 81 | 82 | 83 | 84 | 85 | 86 |
| Phe | Glu | Gly | Lys | Asn | Cys | Glu | Leu | Asp | Val |
| 87 | 88 | 89 | 90 | 91 | 92 | 93 | 94 | 95 | 96 |
| Thr | Cys | Asn | Ile | Lys | Asn | Gly | Arg | Cys | Glu |
| 97 | 98 | 99 | 100 | 101 | 102 | 103 | 104 | 105 | 106 |
| Gln | Phe | Cys | Lys | Asn | Ser | Ala | Asp | Asn | Lys |
| 107 | 108 | 109 | 110 | 111 | 112 | 113 | 114 | 115 | 116 |
| Val | Val | Cys | Ser | Cys | Thr | Glu | Gly | Tyr | Arg |
| 117 | 118 | 119 | 120 | 121 | 122 | 123 | 124 | 125 | 126 |
| Leu | Ala | Glu | Asn | Gln | Lys | Ser | Cys | Glu | Pro |
| 127 | 128 | 129 | 130 | 131 | 132 | 133 | 134 | 135 | 136 |
| Ala | Val | Pro | Phe | Pro | Cys | Gly | Arg | Val | Ser |

Sequence of amino acid residues 43-136 which comprises the EGF domain (47-136) of human Factor IX and the four residues(43-46) immediately preceding this portion. The amino acids aredesignated by their common three letter abbreviations. Above each amino acid designation is the number that the residueoccupies in the sequence of the entire Factor IX molecule.

In this regard, it will be noted that the EGF domain of human Factor IX is not identical to the corresponding fragment of bovine Factor IX. Each comprises 90 residues, and of these there are 13 residues which are different (See FIGS. 1 and 2). It will be understood that the peptides of the present invention need not be species specific, although this is preferred.

The peptides of this invention may be produced by peptide synthesis methods either in solution or solid phase. Also, peptides may be produced using recombinant DNA techniques wherein natural genes code for a selected amino acid sequence.

A preferred method for producing the peptides is a modification of the solid phase technique of Merrifield, (Biochem. 3, pp. 1385-1390 [1964]), as described by Wilner, et al. (Biochem. 15, pp. 1209-1213 [1976]). Synthesis preferably is carried out on a microcomputer-controlled automated synthesizer, such as a Vega Model 1000.

In the preferred method, the solid phase synthesis is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin, or via an amide bond to a benzhydrylamine (BHA) resin or methylbenzhydrylamine (MPHA) resin. These resins are commercially available.

Cleavage and deprotection of the fully protected peptide resins next is performed. Preferably, these procedures are carried out using anhydrous hydrogen fluoride in the two-step procedure described by Tam, et al. (J. Am. Chem. Soc., 105, pp. 6442-6455 [1983]). Other suitable methods for protecting and removing protecting groups from amino acid are described in The Peptides, Vol. 2 (E. Gross and J. Meienhoffer, eds., Academic Press, New York [1979] at pp. 1-284). Exemplary protecting groups include tert-butyloxycarbonyl (Boc), benzyl (Bzl), 2-chlorobenzyloxycarbonyl (2 Cl-Z) and 3, 4-dimethylbenzyl (Dmb) groups.

After removal of the α-amino protecting group from the initial (C-terminal) amino acid, the remaining protected amino acids are coupled step-wise in the desired order. The entire peptide may be synthesized in this way. Alternatively, small polypeptides may be constructed which are later joined, to give the final peptide product. Among several appropriate coupling reagents, dicyclohexylcarbodiimide (DCC) is particularly suitable.

Each protected amino acid or peptide is introduced into the solid phase reactor in excess, and the coupling may be carried out in a medium of dimethylformamide (DMF) or methylene chloride ($CH_2C_{12}$), or mixtures thereof. In cases where incomplete coupling occurs, the coupling procedure is repeated before removal of the N-amino protecting group prior to the coupling of the next amino acid. The success of the coupling reaction at each stage of synthesis may be monitored. A preferred method of monitoring the synthesis is by the ninhydrin reaction. The coupling reactions and washing steps can be performed using automated instrumentation.

Cleavage of the peptide from the resin can be effected using established procedures. For example, reaction with hydrogen fluoride in the presence of p-cresol and dimethylsulfide at 0° C. for 1 hour may be followed by a second reaction with hydrogen fluoride in the presence of p-cresol for 2 hours at 0° C.

Purification of the polypeptides of the invention may be achieved using procedures including but not limited to gel permeation (filtration), isoelectric focusing, ion exchange and partition chromatography or countercurrent distribution. Preparative HPLC is especially preferred using a spherisorb ODS (2.5×25 cm) column and eluted with a 0.025% trifluoroacetic acid/water-acetonitrile gradient.

The purified protein product may be combined with a pharmaceutically acceptable carrier to make a pharmaceutical composition. The composition may be prepared for oral, topical or parenteral administration. In many instances, such as where the subject is or has been undergoing fibrinolytic therapy, the intravenous route will be preferred. In other instances, such as where small peptides are used, enteric coated or polymer encapsulated oral formulations may be employed. Also, it will be noted that the peptides of this invention may be lyophilized for reconstitution with sterile water or saline.

It will be understood that the carrier selected and the concentration of the composition will depend upon the route of administration to be used, and may be determined using standard procedures. Therapeutic levels may be determined also using standard procedures.

The following examples illustrate the practice of the present invention.

EXAMPLES

1. Synthesis and purification of peptides

Two synthetic peptides first were prepared: (1) Asp-Gly-Asp-Gln-Cys corresponding to residue nos. 46–51 of both the human and bovine Factor IX molecules; and (2) Lys-Gln-Tyr-Val-Asp-Gly-Asp-Gln-Cys, corresponding to residue nos. 43–51 of the human Factor IX. The peptides were synthesized by a modification of the solid phase method of Merrifield as described by Wilner, et al. (Biochem. 15, pp. 1209–1213 [1976]). Synthesis was carried out on a microcomputer controlled Vega Model 1000 automated synthesizer. Cleavage and deprotection of the fully protected peptide resins was carried out with anhydrous fluoride using the two-step procedure described by Tam, et al. (J. Am. Chem. Soc., 105, pp. 6442–6455 [1983]).

The purification of the crude deprotected peptides was accomplished by high pressure liquid chromatography (HPLC) using a Spherisorb ODS-1 (2.5×25 cm) column that was eluted with a 0.025% trifluoroacetic acid (TFA) water-acetonitrile gradient. The purity of the products was shown to be >95% by analytical high pressure liquid chromatography, and the amino acid compositions were confirmed by amino acid analysis.

Further purification of the above peptides to homogeneity was carried out using a Nucleosil $C_{18}$ (5μ) column (1×50 cm) which was eluted with a solvent system consisting of water and $CH_3CN$ (both containing 0.025% TFA), in a linear gradient ranging from 5–25% of the $CH_3CN$ over 140 minutes, with a flow rate of 3 ml/min. Three milliliter fractions were collected, and aliquots were analyzed by the analytical HPLC system. Fractions containing the peptides were pooled, evaporated and lyophilized.

2. In Vitro Binding Studies a. Competitive Binding Capacity of the Peptides.

The purified peptides were tested for their ability to block the binding of bovine Factor IX and IXa to cultured bovine aortic endothelial cells. Bovine Factor IX and IXa for these studies were prepared and radioiodinated (using $Na^{125}I$ and the solid state lactoperoxidase technique) using methods described by Stern, et al. (J. Biol. Chem. 260, pp. 6717–6722 [1985]).

Bovine aortic endothelial cells were obtained from the aortae of newborn calves as described by Stern, et al. (Proc. Natl. Acad. Sci. U.S.A., 80, pp. 4119–4123 [1983]). These endothelial cells were grown to confluence (1.3×10$^5$ cells/cm$^2$) in culture dishes.

Binding assays were carried out by incubating either $^{125}$I-Factor IX or $^{125}$I-Factor IXa with endothelial cell monolayers in the presence of varying concentrations of one of the peptides. The buffer used in these experiments was Minimal Essential Medium containing 0.5 mg/ml transferring, and the incubation time was 4–5 hours at 4° C.

At the end of the incubation period, the cultures were washed to remove unbound material. Then, specifically bound $[^{125}I]$-Factor IX or $[^{125}I]$-Factor IXa was eluted during exposure to EDTA-containing buffer as described by Stern, et al. (Proc. Natl. Acad. Sci. U.S.A., 80, pp. 4119–4123 [1983].

Inhibition of the binding of $[^{125}I]$-Factor IX was observed in competitive binding studies, and these observations are shown in Table I.

TABLE 1

Inhibition of Binding of $[^{125}I]$-Factor IX to Cultured Bovine Aortic Endothelial Cells

| Inhibitor | Inhibitory Constant* |
|---|---|
| Factor IX | 3 nM |
| Factor IXa | 2.5 nM |
| Pentapeptide (Asp-Gly-Asp-Gln-Cys) | 90 μM |
| Nonapeptide (Lys-Gln-Tyr-Val-Asp-Gly-Asp-Gln-Cys) | 100 μM |

The binding studies showed that the two peptides were about equally effective in inhibiting the binding of $[^{125}I]$-Factor IX to the endothelium. However, both peptides were substantially less potent than either Factor IX or Factor IXa.

b. Specificity of the Peptides.

To assess specificity of the peptides, other peptides were tested for their abilities to inhibit the binding of $[^{125}I]$-Factor IX. These other peptides tested included fibrinopeptide A (Ala-Asp-Ser-Gly-Glu-Gly-Asp-Phe-Leu-Ala-Glu-Gly-Gly-Gly-Val-Arg), fibrinopeptide B (PCA-Gly-Val-Asn-Glu-Glu-Gly-Phe-Phe-Ser-Ala-Arg), and Angiotensin I (Asp-Arg-Val-Tyr-Val-His-Pro-Ser-Leu). With up to millimolar amounts of these peptides, no inhibition of $[^{125}I]$-Factor IX endothelial cell binding was observed.

Another pentapeptide, Glu-Gly-Glu-Gln-Cys, wherein the aspartic acid residues were replaced with glutamic acid residues, was also tested. This peptide was ineffective as an inhibitor. Based on this data, it was concluded that the inhibition of Factor IX and Factor IXa binding by the two peptides from the EGF domain of Factor IX is a specific effect.

The two peptides also were tested for inhibitory effect on the binding of radio-labelled Factor X to its endothelial cell cites. In contrast to their ability to inhibit Factor IX binding, neither of the peptides had any inhibitory effect on the binding of radio-labelled Factor X. The binding of Factor X to the endothelial cell surface has been previously demonstrated, as discussed in Heimark, et al. (Biochem. Biophys. Res. Comm. 111, pp. 723–731 [1983]) and Stern, et al (Proc. Natl. Acad. Sci. U.S.A. 81, pp. 913–917 [1984]). Similar results were observed when competitive binding studies were carried out using $[^{125}I]$-Factor IXa as the tracer. Since Factor X is another vitamin K-dependent coagulation factor, the inability of the peptides to compete for binding with this factor further emphasizes the specificity of the action of these peptides with respect to competitive binding with Factor IX.

During the course of these studies, two sets of competitive binding experiments with the pentapeptide (i.e., Asp-Gly-Asp-Gln-Cys) failed. In both these sets, a partially purified material was used. The reason for the failure is not known. However, because results of sets using a more highly purified peptide were consistently successful, it is believed that the failures may have been related to the purification factor.

3. In Vitro Activation Studies

In addition to Factor IX/IXa binding studies, kinetics experiments were carried out to assess the effect of the peptides on endothelial cell-dependent Factors IXa-VIII-mediated activation of Factor X. For these studies, Factor IXa and X were purified by standard methods. Factor VIII was obtained from Genentech (South San Francisco, Calif.).

Endothelial cell monolayers were mixed and incubated with increasing concentrations of one of the peptides in the presence of Factors IXa, VIII and X. The rate of product formation, namely Factor Xa formation, was determined using a chromogenic substrate assay as described by Van Dieijen, et al. (J. Biol. Chem. 256, pp. 3433-3441 [1981]). The results, shown in Table II, indicated that both peptides inhibit Factor X activation.

TABLE II

| Effect of EGF Domain Peptides on Activation of Factor X | |
|---|---|
| Inhibitor | Inhibitory Constant* |
| Asp-Gly-Asp-Gln-Cys | 105 µM |
| Lys-Gln-Tyr-Val-Asp-Gly-Asp-Gln-Cys | 108 µM |

*Inhibitory constants are the mean of experimental values. The standard error of the mean was less than 20%.

It will be noted that the inhibitory constant values for competitive binding with Factor IX (Table I) are similar to the inhibitory constant values for activation of Factor X (Table II). This similarity and the ineffectiveness of the modified pentapeptide Glu-Gly-Glu-Gln-Cys, discussed above, lend support to the hypothesis that inhibition of Factor IX/IXa-endothelial cell binding is the mode of action of the present peptides.

4. In Vivo Studies

Based on the results of the above in vitro studies demonstrating that the peptides of this invention could block Factor IX/IXa-endothelial cell interaction, in vivo studies were conducted. The in vivo model selected was the Wessler stasis venous thrombosis model (Gitel, et al., Proc. Natl. Acad. Sci. U.S.A. 74, pp. 3028-3032 [1977]), and the procoagulant agent was Factor IXa (600 ng). The procedure was performed in rabbits anesthetized with sodium pentobarbital by injecting Factor IXa alone or in the presence of 10 mg of the pentapeptide Asp-Gly-Asp-Gln-Cys. A segment of contralateral jugular vein, which was previously exposed, was isolated by ligating sutures 10 seconds later. Then, after 16 minutes, the isolated vessel was placed in 5% (wt/vol) sodium citrate and opened for inspection of thrombus formation.

Each thrombus was graded on a scale of 0 to 4 as described by Gitel, et al., supra. Animals injected with Factor IXa alone showed a grade 3 thrombus, whereas the animal injected with peptide and Factor IXa showed only a grade 1 thrombus. In one experiment where 8 mg of the pentapeptide were injected into rabbits without Factor IXa, the prothrombin time and activated partial thromboplastin time of citrated blood samples, collected 1, 3, 5 and 10 minutes after peptide infusion, were unchanged.

Based on the foregoing, the present invention provides for the treatment of thrombotic disorders. Peptides made in accordance with the present invention inhibit the pathological thrombotic activity of Factor IX and Factor IXa. Yet, these peptides do not affect the normal coagulation process.

Changes may be made in the nature, composition, operation and arrangement of the various elements, steps and procedures described herein without departing from the spirit and scope of the invention as defined in the following claims.

What is claimed is:

1. A peptide having the formula Asp-Gly-Asp-Gln-Cys which selectively interacts with endothelial cellular receptors for Factor IX and Factor IXa.

2. A peptide having the formula Lys-gln-Tyr-Val-Asp-Gln-Cys which selectively interacts with endothelial cellular receptors for Factor IX and Factor IXa.

3. A pharmaceutical composition comprising a peptide which has the formulas Asp-Gly-Asp-Gly-Cys and selectively interacts with endothelial cellular receptors for Factor IX and Factor IXa and
a pharmaceutically acceptable carrier.

4. A pharmaceutical composition comprising a peptide which has the formula Lys-Gln-Tyr-Val-Asp-Gly-Asp-Gly-Cys and selectively interacts with endothelial cellular receptors for Factor IX and Factor IXa and
a pharmaceutically acceptable carrier.

5. A method for treating thrombotic disorders in a mammalian subject in need of such treatment comprising:
   administering to the subject a therapeutically effective amount of a pharmaceutical composition comprising:
   a peptide having the formula Asp-Gly-Asp-Gln-Cys and selectively interacting with endothelial cellular receptors for Factor IX and Factor IXa; and
   a pharmaceutically acceptable carrier.

6. A method for treating thrombotic disorders in a mammalian subject in need of such treatment comprising:
   administering to the subject a therapeutically effective amount of a pharmaceutical composition comprising:
   a peptide having the formula Lys-Gln-Tyr-Val-Asp-Gly-Asp-Gln-Cys and selectively interacting with endothelial cellular receptors for Factor IX and Fact IXa; and
   a pharmaceutically acceptable carrier.

* * * * *

UNITED STATES PATENT AND TRADEMARK OFFICE
CERTIFICATE OF CORRECTION

PATENT NO. : 4,885,277
DATED : December 5, 1989
INVENTOR(S) : Peter P. Nawroth, David M. Stern, George D. Wilner It is certified that error appears in the above-identified patent and that said Letters Patent is hereby corrected as shown below:

Column 3, line 52, between "Also," and "peptides" insert the word --the--.
Column 4, line 27, change "$(CH_2C_{12})$" to --$(CH_2Cl_2)$--.

Column 5, line 58, change "transferring" to --transferrin--.
Column 6, line 10, after bottom line under the table, insert --The inhibitory constant value is a mean of the experimental values obtained in the competitive binding studies. The standard error of the mean was less than 20%--.
Column 8, line 18, claim 2, delete "Lys-gln-Tyr-Val-Asp-Gln-Cys" and insert in place thereof --Lys-Gln-Tyr-Val-Asp-Gly-Asp-Gln-Cys--.
Column 8, line 50, change "Fact IXa" to --Factor IXa--.

Signed and Sealed this

Tenth Day of May, 1994

BRUCE LEHMAN

*Attest:*

*Attesting Officer*           *Commissioner of Patents and Trademarks*